(12) United States Patent
Bailey et al.

(10) Patent No.: US 8,215,155 B2
(45) Date of Patent: Jul. 10, 2012

(54) RHEOLOGICAL MEASUREMENT OF FILTERCAKE

(75) Inventors: Louise Bailey, Cambridgeshire (GB); Gerald Henry Meeten, Hertfordshire (GB)

(73) Assignee: M-I L.L.C., Houston, TX (US)

( * ) Notice: Subject to any disclaimer, the term of this patent is extended or adjusted under 35 U.S.C. 154(b) by 306 days.

(21) Appl. No.: 12/597,624

(22) PCT Filed: Mar. 19, 2008

(86) PCT No.: PCT/GB2008/000964
§ 371 (c)(1),
(2), (4) Date: Nov. 5, 2009

(87) PCT Pub. No.: WO2008/132425
PCT Pub. Date: Nov. 6, 2008

(65) Prior Publication Data
US 2010/0126252 A1    May 27, 2010

(30) Foreign Application Priority Data
Apr. 26, 2007   (GB) .................................. 0708135.9

(51) Int. Cl.
*G01N 11/14* (2006.01)
(52) U.S. Cl. ..................................................... 73/54.28
(58) Field of Classification Search .................. 73/54.28
See application file for complete search history.

(56) References Cited

U.S. PATENT DOCUMENTS
4,458,528 A   7/1984   Roper et al.
4,601,195 A   7/1986   Garritano

FOREIGN PATENT DOCUMENTS
FR   2 641 868 A   7/1990
GB   2 275 342 A   8/1994

OTHER PUBLICATIONS

International Search Report from PCT/GB2008/000964 dated Jun. 20, 2008 (3 pages).
Written Opinion from PCT/GB2008/000964 dated Jun. 20, 2008 (7 pages).
E.J. La Heij, et al.; "Fundamental Aspects of Sludge Filtration and Expression"; Water Research, Elsevier, Amsterdam, NL; vol. 30, No. 3; Mar. 1, 1996; pp. 697-703 (7 pages).

(Continued)

*Primary Examiner* — Hezron E Williams
*Assistant Examiner* — Rodney T Frank
(74) *Attorney, Agent, or Firm* — Osha • Liang LLP

(57) ABSTRACT

A rheometer is provided for measuring rheological properties of a filtercake. The rheometer comprises a cell for containing a pressurised fluid supporting a particulate suspension. The cell has two outlets for removing the fluid from the cell. The cell further has a respective foraminous body at each outlet, such that the particulate suspension forms a filtercake on a surface of each foraminous body as pressurised fluid filters through the body when the fluid passes from the cell to the respective outlet. The foraminous bodies are translatable relative to each other, such that the filtercakes formed on said surfaces can be approached to form a unified filtercake. The foraminous bodies are also rotatable relative to each other. The rheometer further comprises a torque sensor for measuring a torque required to rotate the foraminous bodies relative to each other. The measured torque is indicative of one or more rheological properties of the unified filtercake.

19 Claims, 4 Drawing Sheets

OTHER PUBLICATIONS

S.J. Lee, et al.; "Consolidation dewatering and centrifugal sedimentation of flocculated activated sludge"; Chemical Engineering Science, Oxford, GB; vol. 58, No. 9; May 1, 2003; pp. 1687-1701 (15 pages).

Howard A. Barnes; "A review of the slip (wall depletion) of polymer solutions, emulsions and particle suspensions in viscometers: its cause, character, and cure"; Journal of Non-Newtonian Fluid Mechanics; vol. 56, pp. 221-251; 1995 (32 pages).

Klaus Wollny; "New Rheological Test Method to Determine the Dewatering Kinetics of Suspensions"; Physica Messtechnik GmbH; Stuttgart, Germany; 2001; pp. 197-202 (6 pages).

Jurgen Tomas et al.; "Compression, Permeation and Flow Behavior of Wet Nanoparticle Cakes, in situ Tested with a Press-Shear Cell"; Chem. Eng. Technol.; 25; pp. 1053-1060; 2002 (8 pages).

RHEOLOGICAL MEASUREMENT OF FILTERCAKE

FIELD OF THE INVENTION

The present invention relates to an apparatus and a method for making rheological measurements of a filtercake.

BACKGROUND OF THE INVENTION

In the drilling of boreholes such as oil or gas wells, a drilling fluid (hereinafter referred to as "drilling mud") is circulated through the well during drilling in order to, inter alia, remove drilled cuttings, balance the pressure of formation fluids to prevent influxes and maintain the stability of the borehole. In order to provide the required density and viscosity, the mud can include certain solids such as barite and bentonite as well as solids derived from the drilling action. When drilling oil and gas wells, it is quite common to encounter subterranean formations which are porous. If the hydrostatic pressure of the drilling fluid is greater than the pressure of fluids in such formations, mud will penetrate the formation. Generally the pore size of such formations is sufficient to admit the liquid components and very fine solids but to filter out the other solids such as barite or bentonite. These filtered solids form on the borehole wall as a filtercake. This filtercake grows and compacts until the differential pressure is balanced by the stress in the filtercake.

The filtercake is typically many times more concentrated than the drilling fluid, and has a shear strength many orders of magnitude greater. It also has a much lower permeability than the formation. Filtercake can therefore be useful as it acts as a barrier to prevent fluid loss from the drilling mud to the formation.

However if the filtercake becomes too thick, problems can occur. For example, filtercake is a significant contributor to differential sticking: if the drill string or bottomhole assembly (BHA) is allowed to rest against the wellbore wall, filtercake can continue to grow around the contact point, and must be yielded in order to free the BHA. Emphasis has therefore been placed on developing thin, highly impermeable but weak filtercakes, which minimise their contribution to severity of differential sticking, and also ease clean-up in the reservoir section.

More recently the focus on sealing fractures to prevent lost circulation of drilling fluids has turned interest towards strengthening and reinforcing filtercakes. As a result, several techniques have been developed to measure filtercake strength and related rheological properties. However, most of these rely on measurements on depressurised cakes, typically by extrusion or "hole punch" methods. These techniques have given robust data consistent with the applied filtration pressure, discriminated between different fluids, and shown the effect of various additives. However, the behaviour of the cake under pressure has remained intractable. The mudcake under pressure can have a higher yield stress, due to possible strain relaxation when the cake is depressurised.

Bailey et al (SPE 39429) disclose a method of measuring the strength of filtercake using a hole-punch or perforation technique. However, the measurement is performed on depressurised filtercakes and therefore does not simulate typical wellbore drilling conditions.

Wollny et al (Applied Rheology 11, 197-202 (2001)) discloses a technique for dewatering a filtercake between a filter and a measuring plate which maintains a zero applied load. A differential pressure is generated across the filter by a vacuum pump, but this method cannot achieve the high pressures typical of well-bore drilling fluids. Rheological properties of the filtercake are measured by oscillating a measuring plate across the filtercake surface.

Tomas and Reichmann (Chem. Eng. Technol. 25 1053 (2002)) discloses an apparatus for the rheological testing of compressed filtercake based on the combination of a compression-permeability cell with a ring shear tester. A filtercake is formed on a filter by filtering a mud in a ring chamber. A ring piston is used to apply a compressive force and to measure the filtercake shear strength. However, this apparatus is not suitable for small samples and/or thin filtercakes.

UK Patent application GB 2275342 A discloses an apparatus and method for measuring the sticking tendency of drilling mud. The apparatus comprises a modified API-specified HPHT half-area filter press, containing a porous surface and a stainless steel ball adjacent to the porous surface. The filter press is filled with a mud to be tested and pressurised with nitrogen. The mud filters through the porous surface under pressure to form a filtercake on the porous surface, the filtrate leaving the filter press through a drain. The filtercake grows around a part of the ball which contacts the porous surface. The ball is then rotated about an axis normal to the porous surface and its resistance to rotation is measured to give an indication of the sticking tendency of the mud. In this device, there is no means to vary the thickness of the filtercake formed between the filter and the ball.

SUMMARY OF THE INVENTION

The present invention provides a rheometer and method for testing filtercakes that allow measurements to be made under a high applied pressure. A high pressure allows closer simulation of wellbore drilling conditions. Further, the present invention is at least partly based on the realisation that by providing two filtering surfaces on which filtercake can form, wherein the separation between the surfaces is adjustable, it is possible to measure rheological properties of a filtercake of different thicknesses.

In a first aspect, the present invention provides a rheometer for measuring rheological properties of a filtercake, the rheometer comprising a cell for containing a pressurised fluid supporting a particulate suspension, the cell having two outlets for removing the fluid from the cell, and the cell further having a respective foraminous body at each outlet, such that the particulate suspension forms a filtercake on a surface of each foraminous body as pressurised fluid filters through the body when the fluid passes from the cell to the respective outlet, wherein the foraminous bodies are translatable relative to each other, such that the filtercakes formed on said surfaces can be approached to form a unified filtercake, and wherein the foraminous bodies are rotatable relative to each other; and the rheometer further comprising a torque sensor for measuring a torque required to rotate the foraminous bodies relative to each other, the measured torque being indicative of one or more rheological properties of the unified filtercake.

Advantageously there does not need to be a fixed standoff between the two foraminous bodies. Further, a controlled compressive force may be applied to the unified filtercake between the two foraminous bodies, in particular during measurement.

Using this apparatus, measurements may be made on filtercakes of different thicknesses, including, for example, very thin filtercakes. Thus the apparatus is suitable for use with small mud samples.

Another advantage is that the filtercake is grown on each of the foraminous body surfaces between which the filtercake is sheared when the bodies are rotated relative to each other.

In this way, a good frictional contact between the filtercake and each of the surfaces may be obtained. Thus slip at the interface between the bodies and the intervening filter cake, which is a well-known source of error in rheological measurement (H. A. Barnes, *A Review of the slip (wall depletion) of polymer solutions, emulsions and particle suspensions in viscometers: its cause, character, and cure*, J. Non-Newtonian Fluid Mechanics, vol. 56, 1995, 221-251), can be reduced or eliminated.

The rheometer may further comprise pressurising means for pressurising the fluid contained in the cell. The pressurising means may be a source of pressurised gas, the cell having an inlet for introducing the pressurised gas into the cell. In this way, a filtercake may be formed on a foraminous body under conditions similar to those encountered when drilling a well through a permeable formation. That is, a differential pressure may be generated across each foraminous body, between the cell and each outlet, which is similar to the differential pressure typically present, for example, between a drilling fluid in a wellbore and the near-wellbore pore pressure. A pressure meter may be provided for measuring the pressure of the fluid in the cell.

The rheometer may further comprise a motor for rotating the foraminous bodies relative to each other. This enables, for example, the unified filtercake between the two foraminous bodies to be sheared at a constant and/or controlled rate.

One of the foraminous bodies may be mounted on the end of a hollow shaft which forms the respective outlet for removing the fluid from the cell, the shaft sealingly penetrating a wall of the cell and being slidably movable in its longitudinal direction such that the foraminous body mounted at the end of the shaft can be translated relative to the other foraminous body. The shaft may be rotatable about its longitudinal axis such that the foraminous body mounted at the end of the shaft can be rotated relative to the other foraminous body. The other foramious body may be mounted over a passage penetrating a wall of the cell, the passage forming the respective outlet for removing the fluid from the cell. Thus the position of one foraminous body may be fixed, while the relative position of the other foraminous body may be controlled from the exterior of the cell, by translating or rotating the hollow shaft.

The foraminous bodies may be porous bodies such as porous metal frits. A particular advantage in using a porous metal frit as the foraminous body is that a high friction contact can be generated between the filtercake and the frit. This is partly due to the surface roughness of the porous metal frits, and partly due to some internal filtercake formation (i.e. within the pores of each frit).

The opposing surfaces of the foraminous bodies may be substantially flat. Preferably, the opposing surfaces of the foraminous bodies are parallel. This provides a relatively large contact area when the foraminous bodies are brought together. The foraminous bodies may be cylindrical, the cylinder end surfaces forming flat opposing surfaces.

In a further aspect, the present invention also provides the cell of the rheometer of the previous aspect.

The rheometer may be used for measuring rheological properties of a filtercake. In particular, the rheometer may be used for measuring rheological properties of a filtercake formed by a drilling mud.

In another aspect, the present invention provides a method for measuring rheological properties of a filtercake comprising the steps of:
(i) providing a fluid supporting a particulate suspension,
(ii) filtering the fluid under pressure through two foraminous bodies to form a filtercake on a surface of each foraminous body as the fluid filters through the body,
(iii) translating the foraminous bodies relative to each other to approach the filtercakes formed on said surfaces and thereby form a unified filtercake,
(iv) rotating the foraminous bodies relative to each other, and
(v) measuring a torque required to rotate the foraminous bodies relative to each other, the measured torque being indicative of one or more rheological properties of the unified filtercake.

The fluid from which the filtercake is formed may be a drilling mud.

Preferably, each foraminous body is in fluid communication with a drain for removing the fluid filtered therethrough.

Step (iii) of the method may further include applying a compressive load between the foraminous bodies to expel fluid from between the unifying filtercakes and allow the unified filtercake to compact. The compressive load may be maintained during steps (iv) and (v). The compressive load may be applied by the pressure of the fluid. A measurement of the torque required to rotate the foraminous bodies relative to each other may be performed for different compressive loads.

An advantage of using the pressure of the fluid to provide the compressive load on the unified filtercake is that the growth of the filtercake and subsequent rheological measurements may be performed under substantially the same pressure.

The method may be performed using the rheometer of the first aspect. Then, for example, the outlets of the cell of the rheometer can provide drains for removing the fluid filtered through the foraminous bodies.

BRIEF DESCRIPTION OF THE DRAWINGS

Embodiments of the invention will now be described by way of example with reference to the accompanying drawings in which.

DETAILED DESCRIPTION

Figure 1A:
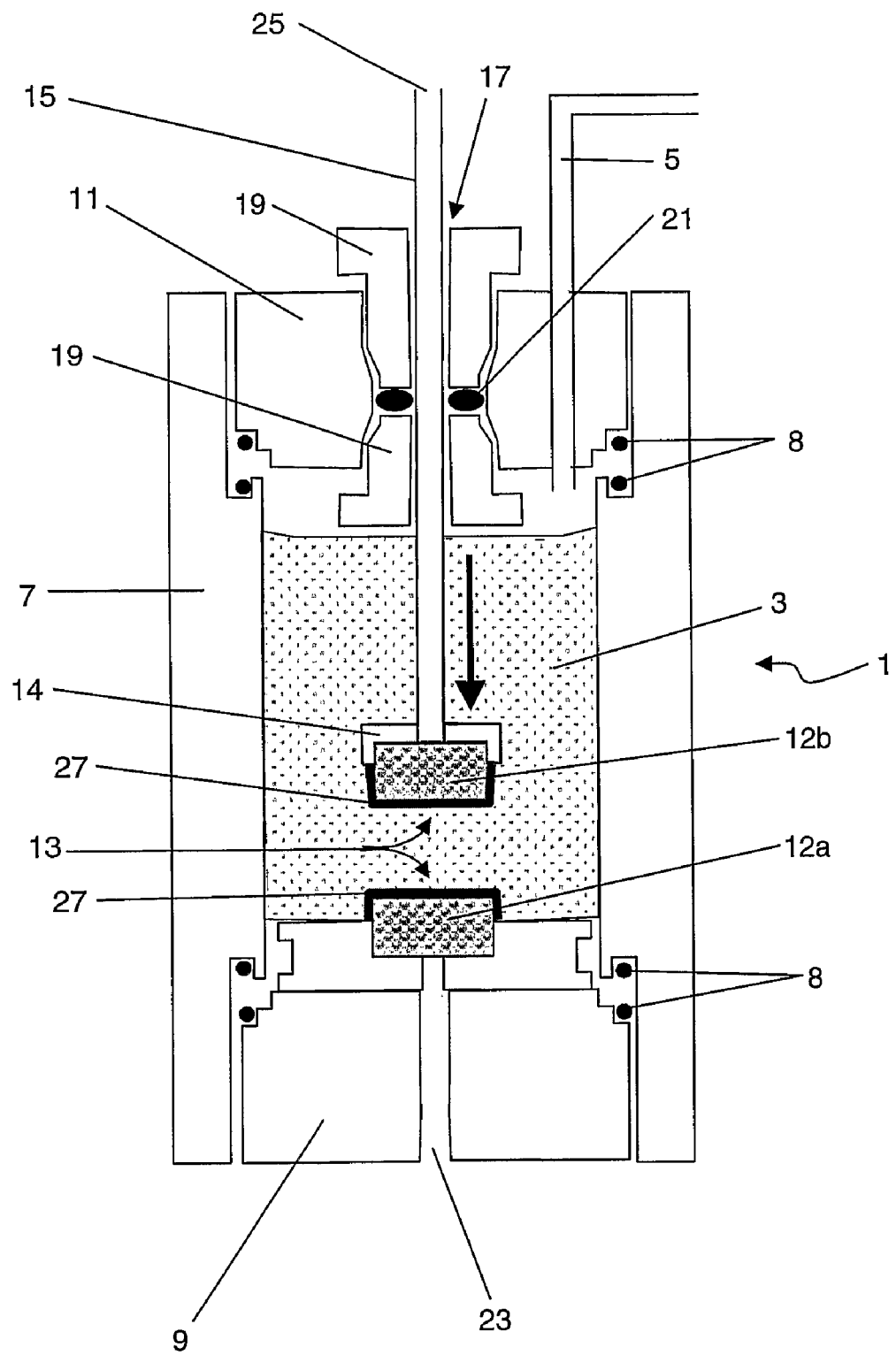
FIGS. 1A and 1B show a filtercake rheometer according to an embodiment of the invention.

The filtercake rheometer according to an embodiment of the invention will now be described in detail with reference to FIG. 1A.

The filtercake rheometer comprises a cell 1, suitable for holding a drilling fluid 3 under pressure. In order to reproduce the typical differential pressures which exist in a well bore during drilling, the cell should be able to withstand pressures of up to at least about 1 MPa. The cell may be, for example, a standard A.P.I. (American Petroleum Institute) double-ended high-pressure high-temperature (HPHT) filtration cell, rated to withstand a pressure of up to 2500 psi (~17.3 MPa). In the embodiment shown, the liquid may be pressurised by connecting gas inlet 5 to a source of pressurised gas. Alternatively, the pressurisation may be achieved by other means, for example by using a hydraulic line filled with the fluid 3, instead of the pressurised gas inlet. This may be safer than using pressurised gas for pressures above about 500 psi (~3.45 MPa).

The cell 1 comprises a cylindrical sidewall 7 and endcaps 9 and 11. Nitrile rubber O-rings 8 seal the joints between the sidewall 7 and endcaps 9, 11 against the pressurised gas or fluid.

The lower endcap 9 is adapted to hold a foraminous body 12a. A second foraminous body 12b, mounted in a housing 14, is attached to a shaft 15 which passes through an opening 17 in the centre of the upper endcap 11. The opening 17 in the upper endcap 11 is closed by two plugs 19 which hold low friction gas seals 21 (for example, Teflon "Bal-Seals" from Oakwade Ltd). The low-friction gas seals 21 enable the shaft 15 to rotate and slide freely with respect to the upper endcap 11, whilst sealing the cell 1 against the pressurised gas.

The first foraminous body 12a covers an opening 23 in the lower endcap 9 of the cell 1. Thus, when the cell 1 is pressurised, there is a differential pressure across the foraminous body 12a. The shaft 15 is hollow and provides a second opening 25 through its upper end to the exterior of the cell. Thus there is also a differential pressure across the second foraminous body 12b when the cell is pressurised. Therefore, when the cell is filled with a fluid 3 and pressurised, the fluid 3 is filtered by each foraminous body 12a, 12b under a controllable, applied differential pressure.

The foraminous bodies 12a, 12b are substantially cylindrical and have a diameter of 25 mm. The foraminous bodies are arranged such that their flat end surfaces 13 are parallel to and oppose each other so as to provide a relatively large contact area when brought together. A suitable material for the foraminous bodies 12a, 12b, is a metal frit having a 10 μm pore size (available from Aegis Advanced Materials Ltd). The first foraminous body 12a may be glued into place across the opening 23. The second foraminous body 12b is secured to the shaft 15 via its housing 14 so that the shaft 15 and foraminous body 12b rotate and translate together. In this embodiment, the external diameter of the shaft 15 is about 8mm. The housing 14 covers the upper surface of the foraminous body 12b, except for the opening 25 into the shaft.

A method for forming and testing a filtercake shall now be described with reference to the specific embodiment of the rheometer shown in FIGS. 1A and 1B. Initially, there is a separation between the two foraminous bodies, as shown in FIG. 1A. The cell 1 is filled with a fluid 3. The fluid may be, for example, a drilling fluid, which supports a particulate suspension. The fluid 3 covers the exposed surfaces of both of the foraminous bodies 12a, 12b, throughout the growth of the filtercakes and the subsequent measurement process.

The fluid in the cell is pressurised by connecting the inlet 5 to a source of pressurised gas. The fluid pressure forces the second foraminous body 12b up to rest against the upper endcap 11. A stop or a spacer may be added to the shaft 15 or housing 14 respectively, to limit the range of translational movement of the shaft 15. This may be needed if the cell 1 is not completely filled with a fluid 3, to prevent the upper foraminous body 12b from rising out of the fluid 3. The fluid 3 is gradually filtered by the foraminous bodies 12a, 12b under the applied differential pressure, the filtrate being drained from the cell through the openings 23, 25 in the endcaps. As the fluid 3 filters through the foraminous bodies 12a, 12b, a filtercake 27 is formed on the exposed surfaces of each of the foraminous bodies, as shown in FIG. 1A. The filtercake 27 includes some of the solids content of the particulate suspension. As the filtration continues, the filtercake grows and progressively dewaters, becoming denser closer to the surface of the foraminous bodies. The filtercake may be substantially less permeable than the foraminous bodies 12a, 12b, and so the rate of filtration may reduce with filtration time (for an initial fluid volume of 200 ml, typically less than 10 ml of filtrate is removed from the cell during filtercake growth). Typical filtercake growth times are in the range 30-60 minutes.

Figure 1B:
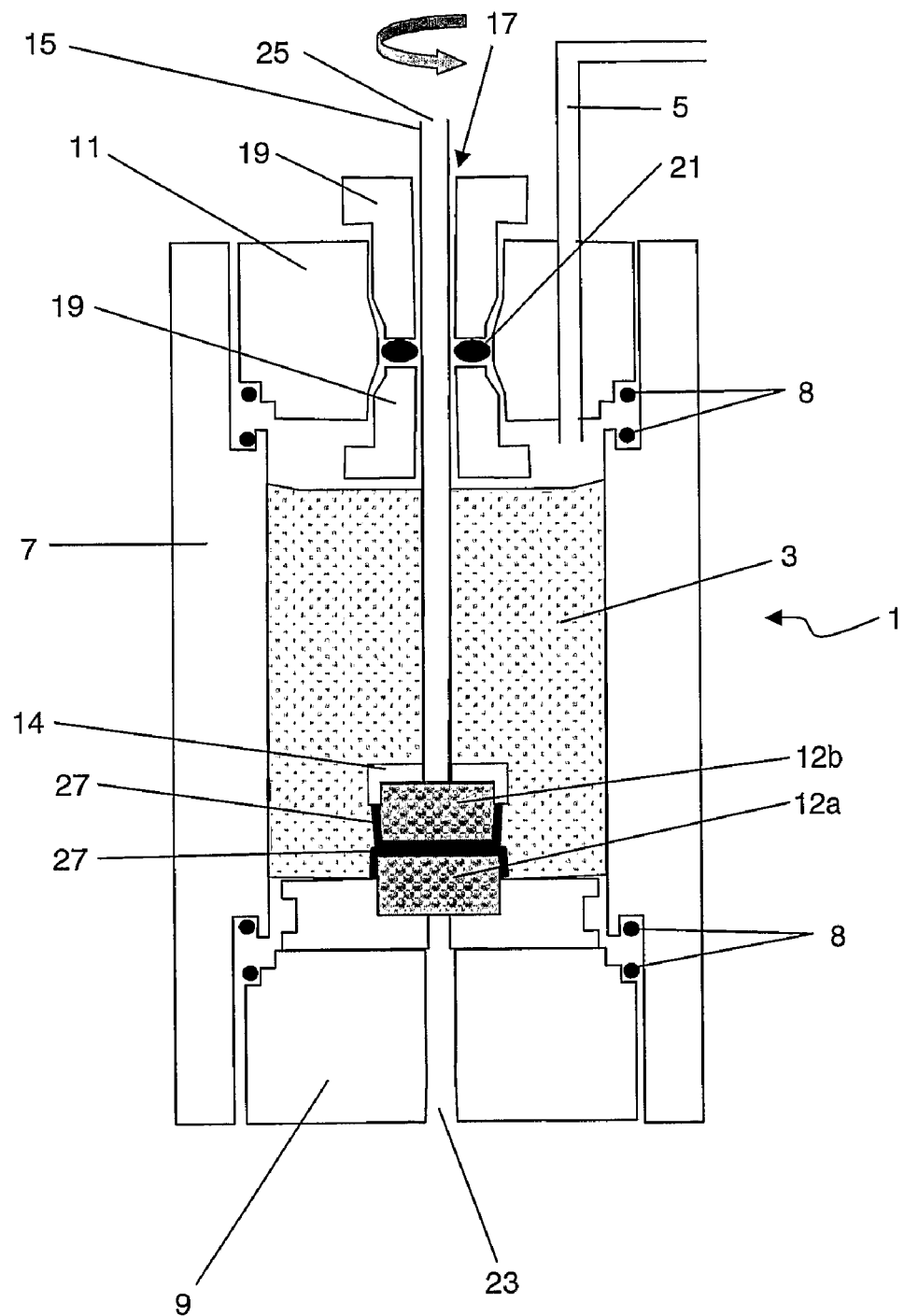

When the filtercake has grown sufficiently, a force is applied to the shaft 15 to translate the upper foraminous body 12b towards the lower foraminous body 12a (see arrow in FIG. 1A). In this way, the two filtercakes are brought into contact or close proximity, as shown in FIG. 1B. The shaft may be temporarily clamped, or held in place by an externally applied force, to maintain a fixed separation between the two foraminous bodies for a period. During this period, typically a few minutes, the film of unfiltered fluid between the two filtercakes dewaters and becomes part of the filtercake, such that the two original filtercakes combine to become a single, unified filtercake. The clamp, or externally applied force, may then be removed from the shaft. The pressure of the fluid 3 on the housing 14 of the upper foraminous body 12a provides a compression force on the filtercake between the two foraminous bodies, which tends to compact and unify the filtercakes. The cake is then left to compact between the foraminous bodies under the pressure of the fluid. However, because the shaft 15 is free to slide, a constant compressive force can be maintained on the filtercake, the separation between the foraminous bodies 12a, 12b reducing as the filtercake compacts. Typically, the filtercake is left to compact for between 30 minutes and 2 hours before a measurement is made on the unified filtercake.

The separation between the two foraminous bodies 12a, 12b, and thus the thickness of the filtercake, may be calibrated and measured by recording the position of the shaft 15.

Rheological properties of the unified filtercake are measured by applying a torque to rotate the shaft 15 (see arrow in FIG. 1B), thereby applying a shear force to the unified filtercake. The torque may be applied manually, or the rotation of the shaft may be driven by a motor. The applied torque is measured using a torque meter (not shown in FIG. 1B) and may be used to derive, for example, the yield stress and/or viscosity of the filtercake. The upper end of the shaft 15 may terminate in a hexagonal screw cap (not shown) for coupling to the torque meter. A support (not shown) may be provided to hold the torque sensor above the cell.

To measure the yield stress of the filtercake, a torque M is applied to the shaft 15, thereby applying a shear force to the filtercake. The torque $M_0$ required to rotate the upper foraminous body is measured. The filtercake yield stress $\tau_0$ can be obtained from the measurement of $M_0$, using the expression:

$$\tau_0 = \frac{12 M_0}{\pi d^3}$$

where d is the diameter of the opposing surfaces 13a, 13b of the foraminous bodies 12a, 12b.

To measure the shear viscosity of the filtercake, a low speed motor may be used to rotate the shaft 15 at a constant angular speed Ω. A torque sensor is used to record both the peak torque $M_0$, required to start the upper foraminous body 12b rotating with respect to the lower foraminous body 12a, and the steady state torque $M_{ss}$ under shear at constant angular speed $\Omega$. The yield stress $\tau_0$ is obtained from $M_0$ as above. In the measurement configuration shown in FIG. 1B, the shear rate varies across the radius of the plate. Hence the steady state torque $M_{ss}$ provides the apparent shear viscosity $\eta_{app}$, from the relation:

$$\eta_{app} = \frac{M_{ss}h}{2\pi\Omega R^4}$$

where h is the filtercake thickness, obtained by measuring the separation between the two foraminous bodies, and R is the radius of the opposing surfaces 13a, 13b.

These rheological measurements can be made at different pressures. Therefore, after performing a first set of measurements at a given fluid pressure, the pressure can be changed and the measurements repeated at a second pressure, and so on. As drilling fluids and their filtercakes are highly thixotropic, it is desirable to wait for an interval between measurements to allow the cake to relax. In making measurements it is preferable to grow the filtercake at the highest pressure and reduce the pressure in stages, as increasing the pressure may further compact the cake altering its material properties. The measurements may also be made for filtercakes having different thicknesses (i.e. for different separations of the two foraminous bodies 12a, 12b). Filtercakes of different thicknesses may be obtained by varying the duration for which the filter cake is grown. Typical filtercake thicknesses are of the order 0.5-3 mm.

EXAMPLES

Figure 2:
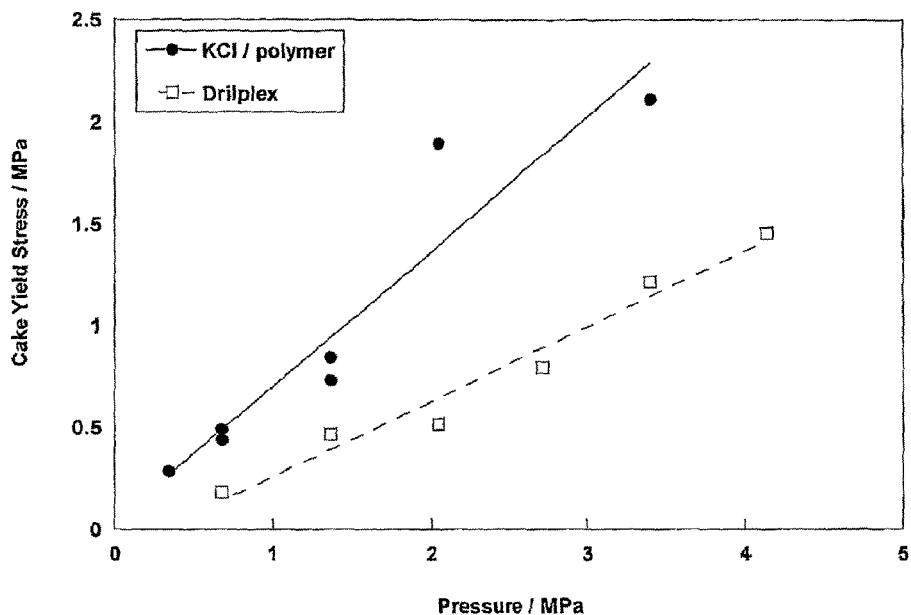
FIG. 2 shows data for yield stress as a function of applied pressure, for water-based drilling muds.
Figure 3:
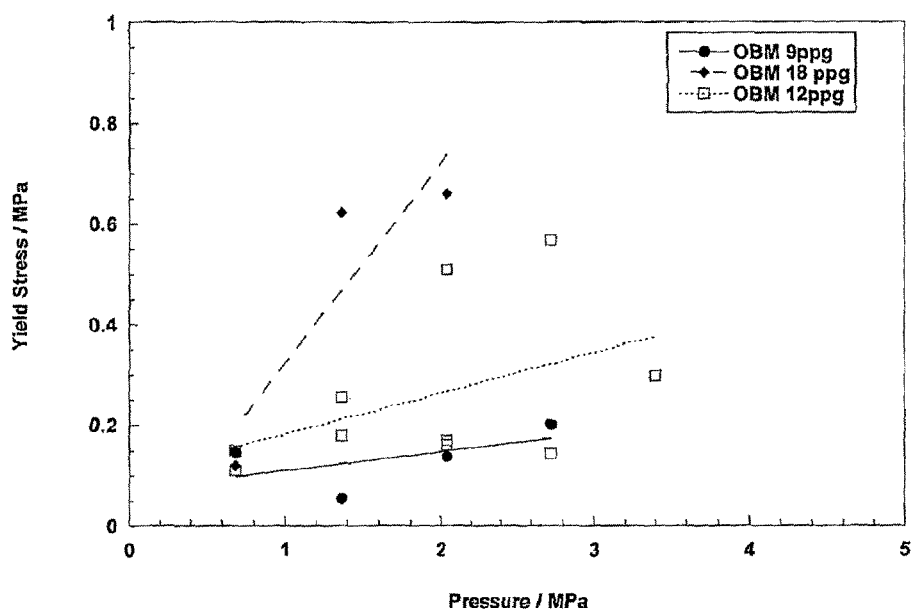
FIG. 3 shows data for yield stress as a function of applied pressure, for oil-based drilling muds.

FIGS. 2 and 3 show typical data for filtercake yield stress as a function of applied fluid pressure. These data were obtained using the method described above, and by manually rotating the shaft 15.

FIG. 2 shows data for filtercakes grown from two water-based muds: KC1-polymer and Drilplex (mmh-bentonite) weighted with barite at 800 g/l. This graph shows that the yield stress has an approximately linear dependence on the applied pressure, with a near-zero intercept. The value of the yield stress lies between 0.1 and 2.5 MPa for applied pressures between 0.2 and 4.5 MPa. The yield stress measured for pressurised filtercakes using this method is significantly higher than comparable data for depressurised filtercakes obtained by other methods. Typical yield stresses measured for equivalent depressurised filtercakes are of the order of only $10^4$ to $10^5$ Pa. This demonstrates an important advantage of this technique, in that the rheological measurements can be carried out under a compression force which is substantially equal to the applied filtration pressure. Thus it is possible to grow filtercakes and to determine their rheological properties at a pressure typical of that of borehole drilling conditions.

FIG. 3 shows data for filtercakes grown from an oil-based drilling fluid weighted with barite to 3 different densities: 9, 12 and 18 ppg. These data show more scatter than the data shown in FIG. 2 for water-based muds.

Figure 4:
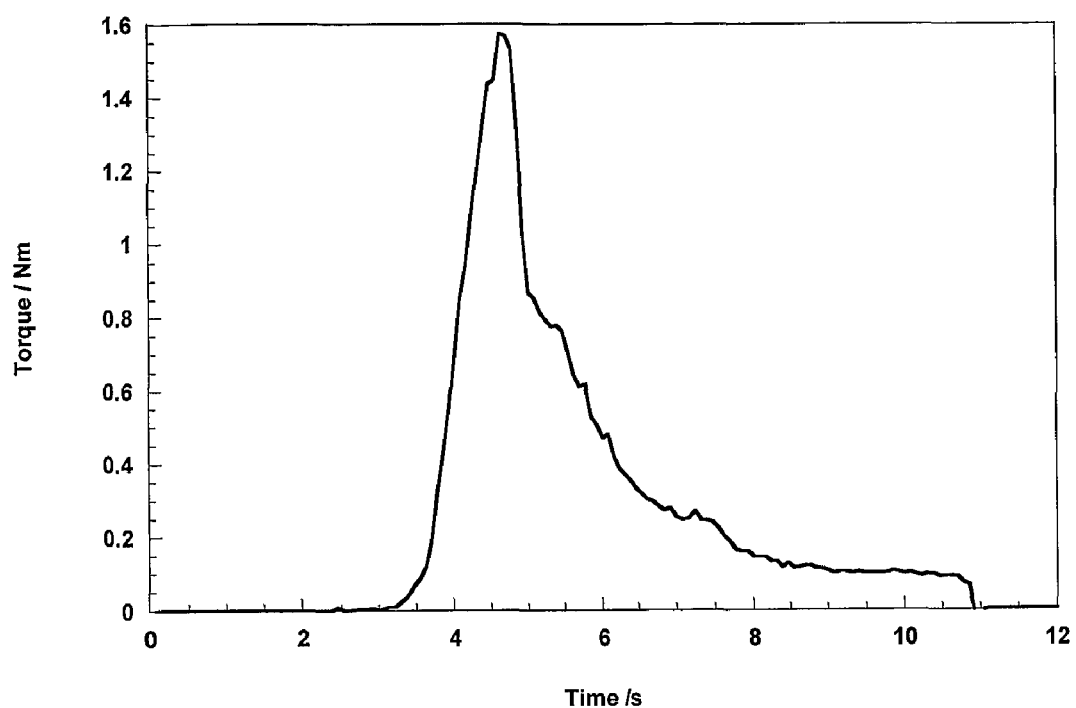
FIG. 4 shows the torque applied to shear a filtercake grown by filtering a water-based drilling mud. The applied pressure is 100 psi (0.69 MPa) and the relative angular velocity of the foraminous bodies, in the steady state is 0.5 rpm (0.052 rad $s^{-1}$).

FIG. 4 shows the time-dependent torque M(t) applied to the shaft 15 to shear a filtercake at a constant angular speed. The filtercake was grown from a KC1-polymer water-based drilling mud weighted with calcium carbonate to a density of 12.5 ppg using a differential pressure of 100psi (~0.69 MPa). A low-speed motor was used to rotate the shaft 15 at a constant angular speed ~0.5 rpm (~0.052 rad s$^{-1}$) at a constant fluid pressure of 100 psi (~0.69 MPa). A torque sensor was used to measure the applied torque M(t) as the shaft was rotated, starting from stationary. Both the peak torque $M_0$ and the steady state torque under shear can be obtained from the graph of FIG. 4. The peak torque $M_0$ of ~1.6 Nm occurs at ~4.6 s and corresponds to a filtercake shear yield stress ~0.4 MPa. The steady state torque of 0.1 Nm, measured at t>9 s, gives an apparent shear viscosity $\eta_{app}$ of ~12.5 kPa s for the filtercake.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references mentioned herein are incorporated by reference.

REFERENCES

1. K. Woliny, New rheological test method to determine the dewatering kinetics of suspensions, Applied Rheology 11 197-202 (2001).
2. J. Tomas and B. Reichmann; Compression, permeation and flow behavior of wet nanoparticle cakes, in situ tested with a press-shear cell, Chemical Engineering and Technology 25, 1053-1060 (2002).
3. P. I. Reid, G. H. Meeten, P. W. Way, P. Clark, B. D. Chambers, and A. Gilmour, Mechanisms of differential sticking and a simple well site test for monitoring and optimizing drilling mud properties, Proceedings of the 1996 IADC/SPE Drilling Conference New Orleans, La., USA, 12-3-1996 IADC/SPE 35100 pp 493-502.
4. C. Klotz, P. H. Beutinger, and P. A. Vermeer, Effects of inherent anisotropy and mode of shearing on the behaviour of geomaterials, 16th Engineering Mechanics Conference, University of Washington, Seattle, USA., 16-7-2003.
5. L. Bailey, G. H. Meeten, P. W. Way, and F. L'Alloret Filtercake integrity and reservoir damage, Proceedings of the 1998 International Symposium on Formation Damage Control Lafayette, La., USA, 18-2-1998, SPE 39429 pp 111-120.
6. G. H. Meeten, S. N. Davies, P. W. Way and C. J. Vercaemer, Apparatus and method for measuring the sticking tendency of drilling mud, UK Patent Application GB 2 275 342 A.
7. UK Patent application GB 2275342 A.
8. H. A. Barnes, J. Non-Newtonian Fluid Mechanics, vol. 56, 1995, 221-251.

The invention claimed is:

1. A rheometer for measuring rheological properties of a filtercake, the rheometer comprising a cell for containing a pressurised fluid supporting a particulate suspension, the cell having two outlets for removing the fluid from the cell, and the cell further having a respective foraminous body at each outlet, such that the particulate suspension forms a filtercake on a surface of each foraminous body as pressurised fluid filters through the body when the fluid passes from the cell to the respective outlet, wherein the foraminous bodies are translatable relative to each other, such that the filtercakes formed on said surfaces can be approached to form a unified filtercake, and wherein the foraminous bodies are rotatable relative to each other; and the rheometer further comprising a torque sensor for measuring a torque required to rotate the foraminous bodies relative to each other, the measured torque being indicative of one or more rheological properties of the unified filtercake.

2. The rheometer according to claim 1, further comprising pressurising means for pressurising the fluid contained in the cell.

3. The rheometer according to claim 2, wherein the pressurising means is a source of pressurised gas, the cell having an inlet for introducing the pressurised gas into the cell.

4. The rheometer according to claim 1, further comprising a pressure meter for measuring the pressure of the fluid in the cell.

5. The rheometer according to claim 1, further comprising a motor for rotating the foraminous bodies relative to each other.

6. The rheometer according to claim 1, wherein one of the foraminous bodies is mounted on the end of a hollow shaft which forms the respective outlet for removing the fluid from the cell, the shaft sealingly penetrating a wall of the cell and being slidably movable in its longitudinal direction such that the foraminous body mounted at the end of the shaft can be translated relative to the other foraminous body.

7. The rheometer according to claim 6, wherein the shaft is rotatable about its longitudinal axis such that the foraminous body mounted at the end of the shaft can be rotated relative to the other foraminous body.

8. The rheometer according to claim 6, wherein the other foraminous body is mounted over a passage penetrating a wall of the cell, the passage forming the respective outlet for removing the fluid from the cell.

9. The rheometer according to claim 1, wherein the foraminous bodies are porous metal frits.

10. The rheometer according to claim 1, wherein the opposing surfaces of the foraminous bodies are substantially flat.

11. The rheometer according to claim 10, wherein the foraminous bodies are cylindrical and the cylinder end surfaces form the flat opposing surfaces.

12. Use of the rheometer of claim 1 for measuring rheological properties of a filtercake.

13. Use of the rheometer of claim 1 for measuring rheological properties of a filtercake formed by a drilling mud.

14. A method for measuring rheological properties of a filtercake comprising the steps of:
  (i) providing a fluid supporting a particulate suspension,
  (ii) filtering the fluid under pressure through two foraminous bodies to form a filtercake on a surface of each foraminous body as the fluid filters through the body
  (iii) translating the foraminous bodies relative to each other to approach the filtercakes formed on said surfaces and thereby form a unified filtercake,
  (iv) rotating the foraminous bodies relative to each other, and
  (v) measuring a torque required to rotate the foraminous bodies relative to each other, the measured torque being indicative of one or more rheological properties of the unified filtercake.

15. A method according to claim 14 wherein the fluid is a drilling mud.

16. A method according to claim 14, wherein step (iii) includes applying a compressive load between the foraminous bodies to expel fluid from between the unifying filtercakes and allow the unified filtercake to compact.

17. A method according to claim 16, further comprising maintaining the compressive load during steps (iv) and (v).

18. A method according to claim 16, wherein the compressive load is applied by the pressure of the fluid.

19. A method according to claim 16, wherein the torque is measured for different compressive loads.

* * * * *